United States Patent [19]

Cromartie

[11] Patent Number: 4,796,610
[45] Date of Patent: Jan. 10, 1989

[54] LATERAL IMPACT KNEE GUARD AND MEDIAL COLLATERAL LIGAMENT KNEE BRACE

[75] Inventor: Hendrick L. Cromartie, Floyd County, Ga.

[73] Assignee: Donjoy, Inc., Carlsbad, Calif.

[21] Appl. No.: 69,503

[22] Filed: Jul. 2, 1987

[51] Int. Cl.[4] ............................. A61F 5/00; A61F 5/04
[52] U.S. Cl. ..................................... 128/80 C; 128/88
[58] Field of Search ................. 128/80 C, 80 R, 80 F, 128/88

[56] References Cited

U.S. PATENT DOCUMENTS

| | | | |
|---|---|---|---|
| 2,308,776 | 1/1943 | Peckham | 128/88 |
| 3,055,359 | 9/1962 | Palmer | 128/80 F |
| 3,786,804 | 1/1974 | Lewis | 128/80 C |
| 4,233,967 | 11/1980 | Daniell, Jr. | 128/80 C |
| 4,249,524 | 2/1981 | Anderson | 128/80 C |
| 4,428,369 | 1/1984 | Peckham et al. | 128/80 C |
| 4,556,053 | 12/1985 | Irons | 128/88 |
| 4,643,176 | 2/1987 | Mason et al. | 128/80 C |

FOREIGN PATENT DOCUMENTS

846895  8/1952  Fed. Rep. of Germany .... 128/80 C

Primary Examiner—Edgar S. Burr
Attorney, Agent, or Firm—Vivian L. Leon

[57] ABSTRACT

A knee guard and brace with a single, laterally-worn side member having elongated thigh and calf support pads each of which is connected by a floating joint to one of two ribs. The ends of these ribs remote from the floating joints are interconnected by a centrally located mechanical joint structure. The floating joint connections between the elongated pads and the ribs are disposed generally in the middle of the pads and are sufficiently flexible to allow each pad to fit snugly, along its entire length, against a wearer's leg when the knee guard and brace is strapped to it. This closeness of fit is achieved without elaborate custom-fitting. Once the knee guard and brace is secured to a wearer's leg, movement of the section of each pad proximate the knee joint inwardly and away from the ribs can be prevented by adjusting the position of spacers rotatably attached to the ribs. Positioning the spacers to accommodate a particular user is readily accomplished by rotating each spacer until it barely touches a bracket mounted on the support pad next to the rib and then fixing the spacer in that configuration. With the spacers so fixed, straps attached to the ends of the support pads proximate the knee can be utilized with these pads to support a knee with a weakened medial collateral ligament against inwardly directed non-contact forces. Moreover, the ribs can deform inwardly essentially independently of the support pads, thereby protecting the knee against contact forces.

8 Claims, 1 Drawing Sheet

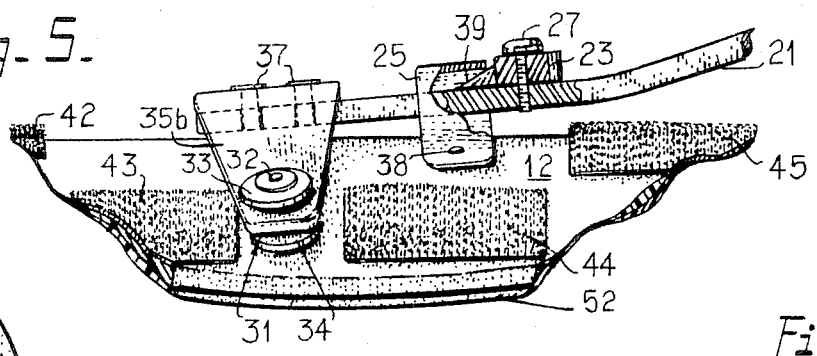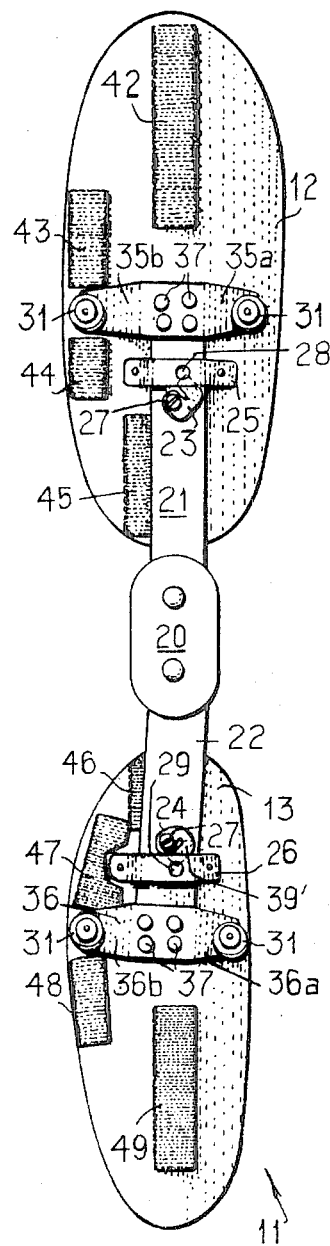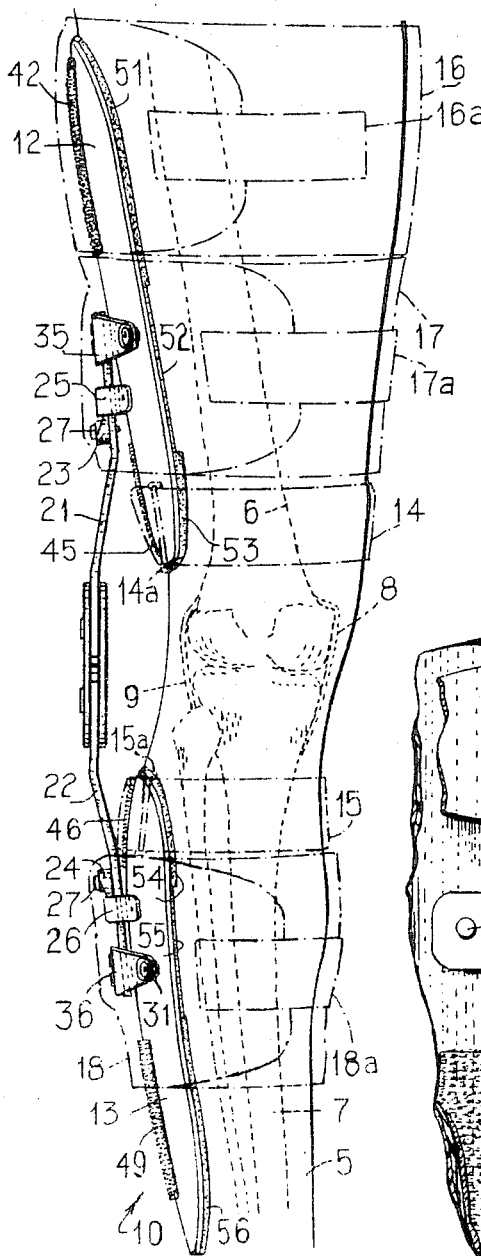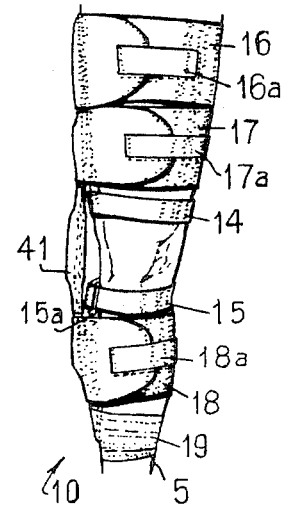

LATERAL IMPACT KNEE GUARD AND MEDIAL COLLATERAL LIGAMENT KNEE BRACE

BACKGROUND OF THE INVENTION

1. Field of the Invention

This invention relates generally to a knee guard and brace having a pair of support pads which are secured to a user's leg by straps and which are connected to longitudinal support ribs which interact with each other within a mechanical joint structure which is worn at the side of a user's knee. More particularly, it relates to such a knee guard and brace in which the ends of the support pads can, during fitting operations, move inwardly and outwardly, to a certain extent independently of the ribs. The invention has specific application in reducing the chance of injury and the extent of damage from a lateral blow to the knee area which an athlete may incur during contact sports and to give aid and support in the rehabilitation of a knee injury, especially one in which the medial collateral ligament of the knee joint has been torn or weakened.

2. Description of the Prior Art

Knee guards and braces having a single, laterally-worn side member with two ribs pivotally connected to a mechanical joint structure which together with it form an arch over the knee joint are known in the prior art. Such knee guards and braces are utilized primarily to protect the knee joint of a wearer from a lateral blow.

Recognizing that the forces from a lateral blow to the arch in the outer side member of a knee guard and brace act on the support pads anchoring the ribs to the thigh and calf and that these forces tend to move the ends of these pads proximal the knee inwardly unless sufficiently strong restraining forces are applied to the ends of the support pads distal the knee, Daniell in U.S. Pat. No. 4,233,967 taught the use of elongated support pads. To magnify the effects of the restraining forces supplied by straps securing the ends of such pads distal the knee, Daniell subsequently extended them longitudinally as far as possible in a direction away from the knee joint and from their junctures with the ribs.

None of the previous knee guards and braces having a single, laterally-worn side member and intended for use in contact sports, however, utilizes elongated support pads which extend longitudinally from their junctures with the ribs both away from the knee joint and into close proximity of it. In the case of knee guards and braces in which the ribs are rigidly attached to the support pads, the amount of custom-fitting required to reshape the ribs and the support pads to accommodate individual differences in the inclination of the femur relative to the tibia would be excessive. Even more troublesome would be the fact that the force of a lateral blow to the arch in such a knee guard and brace causes both the arch and the ends of the pads proximal the knee to deform medially that is, in a direction toward the median plane of the human body, the plane which divides the body lengthwise into symmetrical halves. With the pad ends close to the knee joint, much of the impact of the blow would be sustained by the knee joint itself, abrogating the primary benefit of wearing the knee guard and brace.

On the other hand, knee guards and braces with a single, laterally-worn side member having ribs which are flexibly connected to elongated support pads, although generally not requiring custom-fitting and having less tendency for the ends of the pads proximal the knee to deform medially with the arch, would also be unsuitable, especially for use on a playing field, since these ends of the support pads cannot prevent parts of the knee joint from moving inwardly under the influence of valgusdirected non-contact forces with possible severe injury to the knee. inwardly toward the knee joint could severely injure it. Indeed, knee guards and braces with both lateral and medial side members have, in the past, been considered necessary to prevent injury from valgus-directed non-contact forces. Otherwise, when the knee joint bows inwardly under the influence of non-contact forces, there is no medial side member present to become taut against the knee and thereby reduce the chance of collapse of the joint.

SUMMARY OF THE INVENTION

It is a principal object of the present invention to provide a new and improved knee guard and brace for use in contact sports having a single, laterally-worn side member which not only protects a wearer from lateral blows to the knee joint but which also reduces the likelihood of injury from non-contact forces to the ligaments of this joint, especially the the medial collateral ligament which extends downwardly from the femur to the tibia along the inner side of the knee joint and which is the most frequently injured collateral ligament.

A further object of this invention is to provide a knee guard and brace having only a single, laterally-worn member in which the ends of the support pads proximal the knee extend into close proximity of the knee joint but cannot deviate medially to any significant degree from a configuration corresponding to a state of normal femoral and tibial obliquity for a particular user even while allowing the arch to deform under the impact of a lateral blow.

A still further object of this invention is to achieve in a knee guard and brace having a single, laterally-worn side member a degree of protection for a wearer's knee from ligament injury due not only to lateral blows and to valgus- and varus-directed forces but also to hyperextension and to translocation of the tibia and of either tibial condyle both in an anterior and in a posterior direction.

A still further object of this invention is to achieve protection for a wearer's knee from ligament injury from non-contact forces tending to move either the tibia or the femur medially and to facilitate the rehabilitation of such an injury in part by utilizing elongated support pads in a brace having at least one side member in which its pads extend into the area of the knee joint but can be adapted to the femoral and tibial obliquity of an individual wearer without elaborate custom-fitting.

In accordance with the present invention, there is provided a knee guard and brace comprising a single side member having a pair of elongated thigh and calf support pads adapted to fit on the outside of a wearer's leg, means for securing the pads to the limb, a pair of ribs each of which is connected by at least one floating joint to one of the pads and means including a mechanical joint structure situated between the pads for interconnecting the ribs. The ribs and the mechanical joint structure together form an arch over the side of the knee joint to protect this weakest area of the leg from lateral blows. The arch extends from points which are generally in the middle of the thigh support pad to points which are generally in the middle of the calf support pad. The floating joint between each rib and the pad with which it is paired not only helps to dissipate the impact of lateral blows to the arch so that the end of the pad proximate the knee joint does not deviate medially to a significant degree when the arch deforms with a blow but also facilitates fitting the pad to the wearer's thigh or calf even though the pad extends substantially the length thereof and into close proximity of the knee joint. The pad securing means includes non-yielding straps which together with the ends of the pads proximal the knee can be worn so as to encircle the wearer's leg sufficiently close to the knee to constrain a portion of the ligaments and other tissue therein.

To prevent injury to the ligaments of the knee joint from movement of the knee inwardly and away from the rib under the influence of valgus-directed force there are provided means including a bracket mounted on the pad for limiting the extent to which the section of each pad proximate the knee joint can move medially and independently of the rib connected to the pad and means including a non-yielding strap for securing this section of the pad to a wearer's leg. Protruding outwardly from the pad, the bracket spans the rib between the floating joint connecting it to the pad and the midsection of the arch. The bracket, which is rigidly attached to the pads, abuts a spacer mounted on the proximate rib whenever a valgus-directed force acts on the wearer's knee joint.

To eliminate any movement independent of the ribs in a medial direction of the section of each pad proximate to the knee joint, the position of each of the spacers can be adjusted prior to use. Rotatable about a pivot near one of the brackets, each spacer includes an eccentric arm with a ramp which rises from the surface of the rib. With the wearer in a state of normal femoral and tibial obliquity which may be unique to him, each of the spacers is positioned by simply rotating it until the outer surface of its ramp barely touches the contiguous bracket and then fixing the spacer in that particular configuration. The knee guard and brace with both of its spacers so fixed prevents the ends of the pads proximal the knee from being pulled away from the ribs in a medial direction. Thus, once a wearer secures the pads to his thigh and calf at points near his knee using non-yielding straps, the brace can protect the knee joint from non-contact valgus-directed forces. At the same time, even though the pads extend to points near the knee, the wearer is protected against lateral impact blows to the outside of his knee because the arch formed there by the ribs and the mechanical joint structure can flex inwardly independently of the end sections of the pads proximate the knee.

BRIEF DESCRIPTION OF THE DRAWING

Further details are explained below with the help of the examples illustrated in the attached drawings in which:

FIG. 1 is a side elevational view of a side member of a knee guard and brace according to the present invention in which the side member is designed for use on the right leg;

FIG. 2 is a frontal elevational view of the side member according to FIG. 1 in which the side member is shown strapped to the outside of a wearer's right leg, the straps being illustrated by lines with long dashes and dots;

FIG. 3 is a frontal elevational view on a reduced scale of the knee guard and brace according to the present invention in which the knee guard and brace is shown strapped to a wearer's right leg and the mechanical joint structure is protected by a cover;

FIG. 4 is an enlarged fragmentary section of the side member according to FIG. 1 showing a frontal elevational view of a spacer connected to a rib when the spacer is barely touching a bracket mounted on the support pad nearest the rib, an alternate position of the spacer being superimposed in lines with long dashes and dots; and FIG. 5 is a side elevational view, shown partially in cross-section, of the fragmentary section shown in FIG. 4.

Like reference characters indicate corresponding parts throughout the several views of the drawings.

DESCRIPTION OF THE PREFERRED EMBODIMENT

The present knee guard and brace is designed to protect the ligaments of the human knee joint. The articulating surfaces of this joint offer no restraint to its movements. Rather, restraining ligaments, including the medial and lateral collateral ligaments, indicated generally by the reference numerals 8 and 9, respectively, and the anterior cruciate and posterior cruciate ligaments, are required to restrict the movements of the knee joint to practically one plane while the axis around which motion takes place shifts its position slightly during flection and extension of the joint.

According to reliable studies, the most frequently injured ligament of the knee joint during participation in contact sports such as football is the medial collateral ligament 8. Extending from the inside of the head of the femur to the inside of the head of the tibia, the medial collateral ligament 8 prevents the knee from bowing inwardly. The ligament 8 may be stretched or torn as the result of a lateral impact blow (contact force) to the knee. Once the ligament 8 is so stretched or torn, the ligament must be supported so as to protect it from noncontact forces which may be brought to bear on it during any athletic event and also to guard the knee against further damage from lateral impact blows.

Referring now to the drawings, the present knee guard and brace 10 is shown secured by straps 14, 15, 16, 17, 18 and tape 19 to the right leg 5 of a wearer. As shown in FIGS. 1 and 2, the knee guard and brace 10 comprises a single side member 11 having a pair of elongated thigh and calf support pads 12, 13 flexibly connected to the distal ends of a pair of longitudinal ribs 21, 22, respectively. A mechanical joint structure 20 interconnects the proximal ends of the ribs 21, 22 and together with them forms an arch which spans the area of the knee joint. This arch extends to points which are disposed generally midway within each of the pads 12, 13; and since in use the midpoints of these pads are contiguous with the large muscles of a wearer's thigh and calf, the ends of the arch are also disposed proximate these large muscles. In the preferred embodiment, the joint structure 20 is a polycentric hinge. Other joint structures designed to simulate closely the natural movement of the human knee joint such as those disclosed in U.S. Pat. No. 4,320,747 can obviously be substituted for the structure 20 and such changes are not excluded from the content of this disclosure. The ribs 21, 22 and the structure 20 are preferably formed of a suitable high strength, lightweight material such as a plastic or non-corrosive metal alloy. In the preferred embodiment, the ribs 21, 22 are fabricated from an aluminum alloy and have a transverse cross-section which measures, by way of example, approximately 1⅛ inches by 3/16 inch.

Atop the distal end of each rib 21, 22 is rigidly attached a flanged member 35, 36. Rivets 37 secure the ribs 21, 22 to the members 35, 36. Flanges 35a, 35b; 36a, 36b extend transversely on either side of the longitudinal centerline of the contiguous rib. Each of the flanged members 35, 36 bridges substantially the width of the proximate pad 12, 13 to resist any twisting of the ribs 21, 22 away from the pads even through each of the flanged members is connected to one of the pads by floating joints 31. As shown in FIG. 5, each joint 31 includes a pin with an enlarged head 32, a grommet 33 and a washer 34. Both the grommet 33 and the washer 34 are preferably formed of an elastic material such as rubber or the like. In each floating joint 31, a pair of holes aligned with each other in the flanges 35a, 35b; 36a, 36b and the pads 12, 13 is provided for receiving the pin 32; the grommet, flange, washer and pads are held in assembled relation by the pin.

The floating joints 31 enable the arch formed by the proximal ends of the ribs 21, 22 and the mechanical joint structure 20 to deform medially, under the force of a lateral blow, essentially independently of the pads 12, 13. As a consequence, the pads 12, 13 can be extended a substantial distance from their junctures with the flanged members 35, 36 toward the knee without subjecting it to potential trauma from such elongated pads moving medially toward the knee joint while transmitting the impact of a lateral blow to either the ribs 21, 22 or the structure 20.

Furthermore, the floating joints 31 allow the pads 12, 13 to assume a variety of orientations with respect to the ribs 21, 22. This flexibility facilitates fitting the pads 12 and 13 to a wearer's thigh and calf, respectively, even though the pads extend substantially the length of each and the inclination of the femur 6 and of the tibia 7 away from the vertical varies sigificantly between individuals. In the side member 11, the angle between each rib 21, 22 and the longitudinal centerline of the outer surface of the pad 12, 13 which is contiguous to the rib can vary over a wide range; the widths of the ranges of these angles which allow for differences in femoral and in tibial obliquity measure, by way of example, approximately 8 degrees and approximately 6 degrees, respectively. The connections utilizing the floating joints 31 between the elongated pads 12, 13 and the ribs 21, 22 let each pad be fitted snugly, notwithstanding its length, to a user's leg. The flexibility in these connections eliminates the need for custom-fitting the pads or the ribs to a wearer's leg while still providing a close fit between the pads and the limb.

Once the pads 12, 13 have been fitted to a particular individual, however, it is desirable to eliminate any movement of the section of each pad proximate the knee joint which is independent of the rib 21, 22. Means for eliminating such movement in a medial direction includes a bracket 25, 26 protruding outwardly from each pad 12, 13. Each bracket 25, 26 which is affixed to the pad 12, 13 by rivets 38 spans the proximate rib 21, 22 between the flanged member 35, 36 and the structure 20 to limit the travel of the pad 12, 13 medially but only to a certain extent. Means for eliminating such movement altogether comprises a spacer 23, 24 rotatably mounted on each rib 21, 22 and having an eccentric arm with a ramp 39, 39' which can be moved between the bracket 25, 26 and the contiguous rib. By positioning the ramp 39, 39', which in the preferred embodiment has a slope of approximately 14 degrees, between the bracket 25, 26 and the rib 21, 22, respectively, one can reduce the range over which the angle between each rib and the longitudinal centerline of the outer surface of the pad 12, 13 which is contiguous to the rib vary. This range is reduced, by way of example, by as much as 4 degrees in the preferred embodiment. Any remaining flexibility in the movements between the proximal sections of the pads 12, 13 and the ribs 21, 22, once the position of each spacer 23, 24 is properly adjusted prior to use, allows only for such movements in a lateral direction and that only to a very limited extent.

Rotatable about a pivot 27 which, in the preferred embodiment, is also a locking means, each of the spacers 23, 24 is moved until the outer surface of its ramp 39 barely touches the contiguous bracket 25, 26. Two different positions of the spacer 23 are illustrated in FIG. 4; the position shown in dashed lines if for an individual having more femoral obliquity than the individual whose spacer position is shown in solid lines. Once each spacer 23, 24 is aligned to suit the normal femoral and tibial obliquity of a particular wearer; the locking means is then applied; in the case of the preferred embodiment, locking is achieved by simply tightening the screw comprising the pivot until the body of the spacer which is preferably formed of an aluminum alloy or the like is forced slightly into the rib which is preferably fabricated from the same material. Alternately, the positions of the spacers 23, 24 can be fixed by applying a cement such as methyl methacrylate which cures in 5 to 10 minutes through holes 28, 29 in the brackets 25, 26. The knee guard and brace with both of its spacers 23, 24 so fixed prevents the proximal ends of the pads from pulling or being pushed away from the ribs 21, 22.

As shown in FIGS. 1, 2, 4 and 5, each of the support pads 12, 13 includes a rigid outer shell backed by sections of padding 51, 52, 53; 54, 55, 56. Each outer shell has curvature in both a transverse and a longitudinal direction to simulate the natural curvature of the limb so that the pads 12 and 13 can accommodate the large muscles of a wearer's thigh and calf, respectively. The shell is preferably fabricated of a plastic such as polyethylene or the like which measures, by way of example, approximately 0.15 inch in thickness. The padding sections 51, 56; 53, 54 disposed at the distal and proximal ends, respectively, of the pads are preferably at least as thick as the shell and are generally about twice as thick as are the middle padding sections 52, 55. This padding configuration helps to reduce any tendency for either of the pads 12, 13 to rock about a transverse axis passing through the centers of the joints 31 connecting the pad to the proximate rib 21, 22.

Faces 42, 43, 44, 45; 46, 47, 48, 49 of Velcro TM-type cloth fasteners are attached to the pads 12, 13; strips of material (not shown) which mesh with these faces to complete a cloth fastener are stitched to the inner surfaces of the straps 14, 15, 16, 17, 18 so that they can be secured to the pads 12, 13. The straps 16, 17, 18 are preferably fabricated of an elastic material to allow freedom of movement of the large muscles of the wearer's limb. The inner surface of each of these straps 16, 17, 18 has a patterned. soft rubber-like texture to reduce any tendency of the straps to slip and to allow for a user's skin to breathe. The outer surface of each of the straps 16, 17, 18, on the other hand, is formed of a material which can be fastened to the segments 16a, 17a, 18a, each of which is stitched to an end of a proximate strap. The segments 16a, 17a, 18a have faces (not shown)

which are similar to the faces affixed to the pads 12, 13; and these faces of the segments mesh with the outer surfaces of the straps to form Velcro TM-type cloth fasteners.

In order to prevent the side member 11 from sliding down a wearer's leg, tape 19 is prferably wrapped about the distal end of the pad 13 (FIG. 3). Because of the downward extension of the pad 13, its distal end can be anchored, using the tape 19, near the bony structure of the leg below the large muscles of the calf.

Means for securing the proximal sections of the pads 12, 13 to a wearer's leg include straps 14, 15. The straps 14, 15 are fabricated of a non-yielding material to prevent the ends of the femur 6 and of the tibia 7 from moving relative to the pads 12, 13, respectively, and possibly injuring the knee joint, especially the medical collateral ligament 8. By wearing the straps 14, 15 close to the knee joint as illustrated in FIGS. 2 and 3, a user also realizes a degree of protection from hyperextension and from translocations of the tibia 7 and of either tibial condyle both in an anterior and in a posterior direction due to anterior and to posterior cruciate ligament insufficiently, respectively. Each of the straps 14, 15 further comprises a keeper 14a, 15a disposed at one end thereof. In securing the straps, the opposite end of each strap 14, 15 is passed through the keeper 14a, 15a, respectively, and pulled back across itself. A face (not shown) of a Velcro TM-type cloth fastener is brought into contact with a strip of material with which it can mesh to complete the fastener when the strap has been pulled sufficiently tight. This strip of meshing material is situated along substantially the entire length of the side of the strap 14, 15 not secured to the face 34, 46 to facilitate fitting the strap about a user's limb.

In order to prevent binding, sections of a thin padding (not shown) formed of fabric may be secured to the straps 14, 15 along a portion thereof which comes into contact with the back of a wearer's knee. In addition, padding is supplied by the straps 16, 17, 18, which are preferably wrapped twice around the leg. Further, a padded cover 41 formed of thick, flexible material may be employed to surround the structure 20 and cushion lateral blows to it as well as prevent the intrusion of fingers and of other foreign objects therein.

What is claimed is:

1. A knee guard and brace, which comprises:
    (a) a side member which is adapted to fit on the outer side of a wearer's leg, the side member having a pair of thigh and calf support pads, each support pad including an elongated, generally rigid shell which extends approximately the length of the pad of which the shell is a part;
    (b) means situated generally between the pads for interconnecting the ribs, the ribs and the interconnecting means forming an arch over the side of the knee;
    (c) first means for flexibly connecting one end of a first rib to the thigh support pad at at least two points thereon which are transversely spaced from each other and which are disposed generally midway between the endpoints of the thigh support pad, any movements of end sections of the thigh support pad distal from each other occurring simultaneously but alternately inwardly and outwardly about an imaginary line connecting said two points on the thigh support pad, a first end section of the thigh support pad which is disposed proximate to the knee moving away from the first rib when the first end section is moved inwardly and said first end section moving toward the first rib when the first end section is moved outwardly;
    (d) second means for flexibly connecting one end of a second rib to the calf support pad at at least two points thereon which are transversely spaced from each other and which are disposed generally midway between the endpoints of the calf support pad, any movements of end sections of the calf support pad distal from each other occurring simultaneously but alternately inwardly and outwardly along an imaginary line connecting said two points on the calf support pad, a second end section of the calf support pad which is disposed proximate the knee moving away from the second rib when the second end section is moved inwardly and said second end section moving toward the second rib when the second end section is moved outwardly, so that the first and second connecting means not only help to dissipate the impact of any lateral blows to the arch but also allow for adjustments in the orientation of each pad relative to the contiguous rib to accommodate differences between individual wearers in the inclination of the femur relative to the tibia;
    (e) first means mounted on the thigh support pad generally between the ends of the first rib but not connected thereto for limiting the extent to which the first end section of the thigh support pad can move inwardly independently of the first rib;
    (f) second means mounted on the calf support pad generally between the ends of the second rib but not connected thereto for limiting the extent to which the second end section of the calf support pad can move inwardly independently of the second rib, the first and second ribs disengaging from said first and second limiting means, respectively, under the impact of a lateral blow to the arch, so that the arch can deform inwardly essentially independently of the first and second end sections of the thigh and calf support pads, respectively; and
    (g) means for securing the pads to the wearer's leg, the securing means including a pair of straps for holding said leg against the first and second end sections, so that the femur and the tibia cannot pull away from the thigh and calf support pads, respectively.

2. The knee guard and brace according to claim 1 wherein the first limiting means mounted on the thigh support pad further comprises a first bracket rigidly attached thereto, the first bracket spanning a portion of the first rib which is spaced from the outer surface of the thigh support pad when the wearer's leg is in at least one state of femoral and tibial obliquity which is normal for him, and wherein the second limiting means mounted on the calf support pad further comprises a second bracket rigidly attached thereto, the second bracket spanning a portion of the second rib which is spaced from the outer surface of the calf support pad when the wearer's leg is in said state.

3. The knee guard and brace according to claim 2 which further comprises means attached to the first rib for reducing the distance by which the portion of the first rib spanned by the first bracket is spaced from the outer surface of the thigh support pad until the first end section of the thigh support pad proximate the knee cannot move away from the first rib when the wearer's leg is in said state while allowing the first rib to move inwardly and toward the first end section of the thigh support pad, and which further comprises means attached to the second rib for reducing the distance by which the portion of the second rib spanned by the second bracket is spaced from the outer surface of the calf support pad until the second end section of the calf support pad proximate the knee cannot move away from the second rib when the wearer's leg is in said state while allowing the second rib to move inwardly and toward the second end section of the calf support pad, so that the arch can deform inwardly essentially independently of the first and second end sections of the pads proximate the knee but each of said first and second end sections cannot deviate inwardly independently of the contiguous rib.

4. A knee guard and brace, which comprises:
(a) a side member which is adapted to fit on the outer side of a wearer's leg, the side member having a pair of elongated thigh and calf support pads;
(b) means for securing the pads to the wearer's leg;
(c) means for flexibly connecting one end of a first rib to the thigh support pad at points which are generally midway between the endpoints thereof and means for flexibly connecting one end of a second rib to the calf support pad at points which are generally midway between the endpoints thereof;
(d) means situated generally between the pads for interconnecting the ribs, the ribs and the interconnecting means forming an arch over the side of the knee;
(e) a first bracket rigidly attached to the thigh support pad, the first bracket spanning a portion of the first rib but not connected thereto, the first bracket limiting the extent to which a first end section of the thigh support pad proximate to the knee can move iwardly and away from the first rib;
(f) a second bracket rigidly attached to the calf support pad, the second bracket spanning a portion of the second rib but not connected thereto, the second bracket limiting the extent to which a second end section of the calf support pad proximate to the knee can move inwardly and away from the second rib;
(g) a first spacer rotatably mounted on the first rib and having a first arm with a first ramp which rises from the first rib and which can be positioned so that the first ramp protrudes into a spacer between the first bracket and the portion of the first rib spanned thereby, the first spacer being rotatable to bring an inclined surface to the first ramp barely into contact with the first bracket when the thigh support pad is secured to the wearer's leg; and
(h) a second spacer rotatably mounted on the second rib and having a second arm with a second ramp which rises from the second rib and which can be positioned so that the second ramp protrudes into a space between the second bracket and the portion of the second rib spanned thereby, the second spacer being rotatable to bring an inclined surface of the second ramp barely into contact with the second bracket when the calf support pad is secured to the wearer's leg.

5. The knee guard and brace according to claim 4 wherein the distance reducing means attached to the first rib further comprises means for fixing the position of the first spacer so that the extent to which the first ramp protrudes into the space between the first bracket and the portion of the first rib spanned thereby, once adjusted, cannot be varied and wherein the distance reducing means attached to the second rib further comprises means for fixing the position of the second spacer so that the extent to which the second ramp protrudes into the space between the second bracket and the portion of the second rib spanned thereby, once adjusted, cannot be varied, so that when the first and second spacers are fixed in position, the first and second end sections of the thigh and calf support pads, respectively, cannot be pulled away from the ribs in a medial direction, thereby preventing possible injury to the knee from such motion.

6. The knee guard the brace according to claim 4 wherein each of the thigh and calf support pads is further characterized as including an elongated, rigid shell which extends approximately the length of the pad of which the shell is a part and which extends into close proximity of the knee and wherein the pad securing means further comprises a pair of straps for securing the first and second end sections of the thigh and calf support pads to the wearer's leg, so that the femur and the tibia, when either is acted upon by a non-contact force, not only cannot pull away from the first and second ribs, respectively, but also cannot pull away from the thigh and calf support pads, respectively, thereby avoiding possible injury to the knee from such pulling.

7. The knee guard and brace according to claim 4 wherein each of the ribs is further characterized as being spaced from said outer surface of the support pad contiguous with the rib; wherein the means for flexibly connecting said one end of the first rib to the thigh support pad further comprises a first pair of floating joints and a first flanged member rigidly attached to said one end of the first rib, the first flanged member extending transversely to the longitudinal centerline of the first rib and bridging substantially the width of the thigh support pad, the flanged member being connected to the thigh support pad by the first pair of floating joints which are situated proximate the outer edges of the first flanged member to resist any twisting of the first rib away from the thigh support pad even though the first rib is spaced therefrom; and wherein the means for flexibly connecting said one end of the second rib to the calf support pad further comprises a second pair of floating joints and a second flanged member rigidly attached to said one end of the second rib, the second flanged member extending transversely to the longitudinal centerline of the second rib and bridging substantially the width of the calf support pad, the second rib and the second flanged member being connected to the calf support pad by the second pair of floating joints which are situated proximate the outer edges of the second flanged member to resist any twisting of the second rib away from the calf support pad even though the second rib is spaced therefrom.

8. A knee guard and brace, which comprises:
(a) a side member which is adapted to fit on the outer side of a wearer's leg, the side member having a pair of elongated thigh and calf support pads;
(b) means for securing the pads to the wearer's leg;
(c) means for flexibly connecting one end of a first rib to the thigh support pad at points which are generally midway between the endpoints thereof and means for flexibly connecting one end of a second rib to the calf support pad at points which are generally midway between the endpoints thereof;
(d) means situated generally between the pads for interconnecting the ribs, the ribs and the interconnecting means forming an arch over the side of the knee;

(e) a first bracket rigidly attached to the thigh support pad, the first bracket spanning a portion of the first rib but not connected thereto;

(f) a second bracket rigidly attached to the calf support pad, the second bracket spanning a portion of the second rib but not connected thereto;

(g) a first spacer rotatably mounted on the first rib which can be positioned so that the first spacer can protrude into a space between the first bracket and the portion of the first rib spanned thereby, the first spacer having a first ramp with an inclined surface, the first spacer being rotatable to bring the inclined surface of the first ramp barely into contact with the first bracket when the thigh support pad is secured to the wearer's thigh; and (h) a second spacer rotatably mounted on the second rib which can be positioned so that the second spacer can protrude into a space between the second bracket and the portion of the second rib spanned thereby, the second spacer having a second ramp with an inclined surface, the second spacer being rotatable to bring the inclined surface of the second ramp barely into contact with the second bracket when the calf support pad is secured to the wearer's calf.

* * * * *